(12) United States Patent
Knopp et al.

(10) Patent No.: US 8,760,636 B2
(45) Date of Patent: Jun. 24, 2014

(54) OBJECT SCANNING AND AUTHENTICATION

(75) Inventors: Kevin J. Knopp, Newburyport, MA (US); Daryoosh Vakhshoori, Cambridge, MA (US); Christopher Brown, Albuquerque, NM (US); Gregory Vander Rhodes, Melrose, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 1749 days.

(21) Appl. No.: 11/837,284

(22) Filed: Aug. 10, 2007

(65) Prior Publication Data

US 2012/0223130 A1 Sep. 6, 2012

Related U.S. Application Data

(60) Provisional application No. 60/837,383, filed on Aug. 11, 2006, provisional application No. 60/839,848, filed on Aug. 24, 2006, provisional application No. 60/843,279, filed on Sep. 8, 2006, provisional application No. 60/843,067, filed on Sep. 8, 2006.

(51) Int. Cl.
*G01N 21/00* (2006.01)

(52) U.S. Cl.
USPC .......................................................... 356/73

(58) Field of Classification Search
USPC ........................... 356/540–552; 340/540–552
See application file for complete search history.

(56) References Cited

U.S. PATENT DOCUMENTS

| | | | |
|---|---|---|---|
| 5,959,296 | A | 9/1999 | Cyr et al. |
| D491,590 | S | 6/2004 | Singer et al. |
| D501,493 | S | 2/2005 | Singer et al. |
| D503,353 | S | 3/2005 | Singer et al. |
| D526,220 | S | 8/2006 | Wildey et al. |
| 2004/0220753 | A1* | 11/2004 | Tabe ............................... 702/32 |
| 2004/0252024 | A1* | 12/2004 | Huey et al. .................... 340/540 |
| 2005/0248759 | A1 | 11/2005 | Wang et al. |
| 2005/0260764 | A1 | 11/2005 | Grigsby et al. |
| 2007/0023521 | A1 | 2/2007 | Wildey et al. |

* cited by examiner

*Primary Examiner* — Tara S Pajoohi Gomez
(74) *Attorney, Agent, or Firm* — Gordon Stewart

(57) ABSTRACT

Disclosed herein are methods and systems for scanning objects and associated substances, where the methods include: (a) using a first electronic device to scan a feature of an object and provide reference information about the object based on the scanned feature, where the feature identifies the object or a substance associated with the object; (b) using a second electronic device to measure electromagnetic radiation emitted from the object and provide sample information about the object based on the measured electromagnetic radiation; and (c) comparing the sample information and the reference information to determine whether the object includes the substance associated with the object.

30 Claims, 5 Drawing Sheets

OBJECT SCANNING AND AUTHENTICATION

CROSS-REFERENCE TO RELATED APPLICATIONS

This application claims priority under 35 U.S.C. §119 to the following applications: U.S. Provisional Patent Application Ser. No. 60/837,383, filed on Aug. 11, 2006; U.S. Provisional Patent Application Ser. No. 60/839,848, filed on Aug. 24, 2006; U.S. Provisional Patent Application Ser. No. 60/843,279, filed on Sep. 8, 2006; and U.S. Provisional Patent Application Ser. No. 60/843,067, filed on Sep. 8, 2006. The entire contents of each of the foregoing applications are incorporated herein by reference.

TECHNICAL FIELD

This disclosure relates to scanning and authenticating objects and substances associated with objects.

BACKGROUND

Scanning devices can be used at airports, government facilities, and in other locations where security and public safety may be at risk. By detecting the presence of explosives and other hazardous materials using scanning devices, transport of, and commerce in, these materials can be interrupted.

SUMMARY

In a first aspect, the disclosure features a method that includes: (a) using a first electronic device to scan a feature of an object and provide reference information about the object based on the scanned feature, where the feature identifies the object or a substance associated with the object; (b) using a second electronic device to measure electromagnetic radiation emitted from the object and provide sample information about the object based on the measured electromagnetic radiation; and (c) comparing the sample information and the reference information to determine whether the object comprises the substance associated with the object.

Embodiments can include one or more of the following features.

The object can include a container that conventionally holds the substance. The container can be at least partially transmissive of the emitted radiation.

The feature can include a feature on the container. The feature can be positioned on a surface of the container. The feature can include a shape of the container. The feature can include a label positioned on the object.

The method can include outputting an electrical signal based on the comparison. The signal can include information about an identity of the object or substance. Outputting can include transmitting a signal over a communication link. The communication link can be a network (e.g., a wireless network, a cellular telephone network, a local area network). The communication link can be a secure communication link.

The method can include displaying information to a person based on the electrical signal. Displaying the information can include displaying a message indicating an alarm condition or a no-alarm condition. The message indicating the no-alarm condition can correspond to the object or substance not appearing on a list of prohibited items. The message indicating the alarm condition can correspond to the object or substance appearing on a list of prohibited items. The message indicating the alarm condition can correspond to a determination that the object does not comprise the substance associated with the object.

The method can include outputting an audio signal based on the electrical signal.

The feature can include a bar code. The feature can include a radio-frequency identification tag. The feature can include an identification number (e.g., a National Drug Code, a European Article Number, a Global Trade Item Number, a Serial Shipping Container Code, a Global Location Number, a Global Returnable Asset Identifier, a Global Individual Asset Identifier, or a Global Service Relation Number). The feature can include one or more alphanumeric symbols on a label. The feature can include one or more images. At least one of the one or more images can be a logo.

Measuring electromagnetic radiation emitted from the object can include directing radiation to be incident on the object, and measuring radiation emitted by the object in response to the incident radiation. The incident radiation can include radiation in at least one of the ultraviolet, visible, and infrared regions of the electromagnetic spectrum. A distribution of the incident radiation can have a center wavelength of 450 nm or less and/or 200 nm or more. A distribution of the incident radiation can have a center wavelength between 200 nm and 400 nm (e.g., between 240 nm and 260 nm).

An intensity of the incident radiation can be 10 mW or less (e.g., 2 mW or less).

The incident radiation can include radiation in at least one of the microwave region, the radiowave region, the terahertz region, the x-ray region, and the gamma ray region of the electromagnetic spectrum.

Providing reference information can include obtaining information from a database based on the scanned feature. The reference information can be based on an infrared absorption spectrum of the object or substance. The reference information can be based on a fluorescence spectrum of the object or substance. The reference information can be based on a Raman spectrum of the object or substance. The reference information can be based on dielectric information about the object or substance. The reference information can include a measured signal intensity at one or more wavelengths from the object or substance. The reference information can include a photobleaching time for the object or substance, where the photobleaching time includes an elapsed time over which an absorption coefficient of the object or substance is reduced to a predetermined value during illumination with incident light. The reference information can include one or more data acquisition parameters related to the object or substance (e.g., an exposure time for the object or substance).

The database can include a list of prohibited substances. The method can include, if the object or substance matches an entry on the list, outputting an electrical signal indicating an alarm condition.

Providing sample information can include determining an infrared absorption spectrum. Providing sample information can include determining a fluorescence spectrum. Providing sample information can include determining a Raman spectrum.

A total elapsed time between a beginning of the scanning and an end of the comparing can be 60 seconds or less (e.g., 30 seconds or less, 10 seconds or less, 1 second or less).

The method can include determining a concentration of the substance, where determining the concentration includes providing reference information that includes an expected emitted radiation intensity from the substance, measuring an emitted radiation intensity from the substance, and comparing the expected and measured intensities to determine the concentration. Comparing the expected and measured intensities can include determining a ratio of the intensities.

The method can include outputting an electrical signal indicating an alarm condition or a no-alarm condition, where the signal is based on the concentration, where the no-alarm condition corresponds to a concentration that differs from a concentration derived from the reference information by less than a predetermined amount, and where the alarm condition corresponds to a concentration that differs from the concentration derived from the reference information by more than a predetermined amount. The concentration derived from the reference information can include a concentration that is conventionally associated with the substance.

The substance can include two or more components, and the method can include determining concentrations of the two or more components based on a comparison between expected and measured intensities of the two or more components. The method can include outputting an electrical signal that indicates an alarm condition or a no-alarm condition, where expected concentrations of the two or more components are derived from the reference information, and where the alarm condition corresponds to a concentration of at least one of the two or more components being larger than its expected concentration. The method can include outputting an electrical signal indicating an alarm condition or a no-alarm condition, where expected concentrations of the two or more components are derived from the reference information, and where the alarm condition corresponds to a ratio of concentrations of the two or more components differing from an expected value of the ratio based on the expected concentrations by more than a predetermined amount.

Measuring electromagnetic radiation can include making multiple measurements of electromagnetic radiation emitted by the object or substance over a total measurement time. The method can include making a first measurement of electromagnetic radiation emitted by the object or substance, and adjusting the total measurement time based on the first measurement. The total measurement time can be reduced based on the first measurement. The first measurement can include a measurement of fluorescence radiation emitted by the object or substance. The first measurement can include a measurement of infrared absorption by the object or substance. The first measurement can include a measurement of a Raman spectrum of the object or substance.

The substance can be a pharmaceutical compound, or a chemical precursor of a pharmaceutical compound. The substance can be an industrial compound. The substance can be a narcotic. The substance can be an explosive. The substance can be an energetic material. The substance can be a household product. The substance can be a portion of a chemical weapon. The substance can be a solid, a liquid, a gel, a slurry, or a gas.

The method can include, before scanning the feature, detecting the presence of the object. Detecting the presence of the object can include exposing a vessel that includes the object to electromagnetic radiation, measuring electromagnetic radiation emitted from the vessel, and detecting the object within the vessel based on the electromagnetic radiation emitted from the vessel. The electromagnetic radiation to which the vessel is exposed can include radiation in at least one of an x-ray region, an ultraviolet region, a terahertz region, an infrared region, a radiowave region, and a microwave region of the electromagnetic spectrum.

In another aspect, the disclosure features a system that includes: (a) a first apparatus configured to scan a feature on an object and provide reference information about the object based on the scanned feature, where the feature identifies the object or a substance associated with the object; (b) a second apparatus configured to measure electromagnetic radiation emitted from the object and provide sample information about the object based on the measured electromagnetic radiation; and (c) an electronic processor configured to compare the sample information and the reference information to determine whether the object includes the substance associated with the object.

Embodiments can include one or more of the following features.

The system can include a housing that includes the first and second apparatus and the electronic processor. The housing can have a hand-held form factor so that the system is a hand-held device. The housing can be a rugged housing configured to protect the first and second apparatus and the electronic processor.

The processor can be shared by the first and second apparatus.

The system can include a display.

The processor can be configured to output an electronic signal to the display based on the comparison. The electronic signal can include information about an identity of the object or substance. The electronic signal can produce a colored region on the display. The signal can indicate an alarm condition or a no-alarm condition. The no-alarm condition can correspond to the object or substance not appearing on a list of prohibited items. The alarm condition can correspond to the object or substance appearing on a list of prohibited items. The alarm condition can correspond to a determination that the object does not comprise the substance associated with the object.

The first apparatus can include a bar code reader. The first apparatus can include a radio-frequency identification tag reader. The first apparatus can include an optical character recognition scanner. The first apparatus can include a graphical scanner.

The second apparatus can include a detector configured to measure infrared radiation absorption by the object or substance. The second apparatus can include a detector configured to measure fluorescence radiation emitted by the object or substance. The second apparatus can include a detector configured to measure a Raman spectrum of the object or substance. The second apparatus can include a detector configured to measure electromagnetic radiation emitted by the object or substance, where the emitted electromagnetic radiation includes radiation in at least one of the gamma ray region, the x-ray region, the ultraviolet region, the visible region, the infrared region, the terahertz region, the microwave region, and the radiowave region of the electromagnetic spectrum.

The first apparatus includes a source configured to direct electromagnetic radiation to be incident on the object. The source can include at least one of a light emitting diode, a laser diode, and a gas laser. The second apparatus can include a source configured to direct electromagnetic radiation to be incident on the object. The source can include at least one of a light emitting diode, a laser diode, and a gas laser.

The incident electromagnetic radiation can include a distribution of radiation wavelengths, and wherein a center wavelength of the distribution is less than 450 nm (e.g., less than 400 nm, less than 300 nm, less than 250 nm). A center wavelength of the distribution can be more than 200 nm. A center wavelength of the distribution ban be between 200 nm and 400 nm (e.g., between 240 nm and 260 nm).

An intensity of the incident electromagnetic radiation can be 10 mW or less (e.g., 5 mW or less, 2 mW or less).

The system can include a storage medium configured to store reference information.

The system can include a communication interface configured to permit communication with one or more devices over a communication link. The communication interface can include a data transmitter and a data receiver. The data transmitter and data receiver can be configured to permit communication over a communication link that includes a network. The data transmitter and data receiver can be configured to permit communication over a communication link that includes a direct connection to one or more devices. The data transmitter and data receiver can be configured to permit a secure connection to one or more devices over the communication link. The data transmitter and data receiver can be configured to transmit and receive data wirelessly.

The processor can be configured to receive data from one or more devices over the communication link from the data receiver. The data can include reference information. The system can include a storage medium, where the data is stored on the storage medium.

A total mass of the system can be less than 3 kg. A maximum dimension of the system can be less than 36 cm.

The system can include a third apparatus configured to measure electromagnetic radiation emitted from the object, where the third apparatus includes a source configured to direct electromagnetic radiation to be incident on the object, and a detector configured to measure electromagnetic radiation emitted by the object. The detector can be at least one of a tomographic detector, an x-ray detector, and a terahertz radiation detector. The processor can be configured to identify a presence of the object within a vessel prior to scanning the feature, based on electromagnetic radiation measured by the detector.

At least some components of the first apparatus are shared by the second apparatus. The shared components can include optical components and/or electronic components.

In a further aspect, the disclosure features a system that includes a housing having a hand-held form factor and including a first apparatus, a second apparatus, and an electronic processor in communication with the first and second apparatus, where the first apparatus is configured so that during operation, the first apparatus scans an identifying feature on an object and provides reference information to the electronic processor about the object based on the scanned feature The second apparatus is configured so that during operation, the second apparatus measures electromagnetic radiation emitted from the object and provides sample information about the composition of the object to the electronic processor based on the measured electromagnetic radiation. The electronic processor is configured so that during operation, the electronic processor compares the sample information and the reference information to determine whether the object comprises a substance conventionally associated with the object.

Embodiments can include one or more of the features of the other systems and methods disclosed herein, as appropriate.

Embodiments can include one or more of the following advantages.

Authentication of an object or substance associated with the object can be performed accurately and rapidly. As such, the scanning systems can be used in a variety of environments where typical blind scanning methods would be too slow, such as in airport security screening and in scanning of pharmaceutical compounds and other industrial materials.

Scanning systems include a storage unit that can store reference information about substances, including a list of prohibited substances. System operators, therefore, do not have to remember which substances are prohibited, and/or which products contain which substances. Because lists of prohibited substances can be lengthy and can change frequently, the scanning systems can eliminate a potential security hole by eliminating system operators from the process of detecting prohibited substances. As an added advantage, the scanning systems can receive updates to stored reference information, including spectral data for substances and lists of prohibited substances, in an automated fashion from a remote computer system or other device, ensuring that each scanning system's reference information database is always up-to-date.

Scanning systems are relatively small, lightweight, and hand-held. Thus, the systems can be used in a variety of environments, including field work, without imposing an undue transportation burden on system operators.

Substances can be scanned through the walls of containers, preventing contact between the system operator and a substance in question. This reduces the health risks to the operator from handling unknown materials. Further, the incident radiation used to scan the substances can be very low power radiation. As such, if the substance in question includes energetic materials that are heat- or light-sensitive, the low power radiation is unlikely to initiate an explosive decomposition.

Unless otherwise defined, all technical and scientific terms used herein have the same meaning as commonly understood by one of ordinary skill in the art. Although methods and systems similar or equivalent to those described herein can be used in the practice or testing of the disclosed techniques, suitable methods and systems are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

Figure 1:
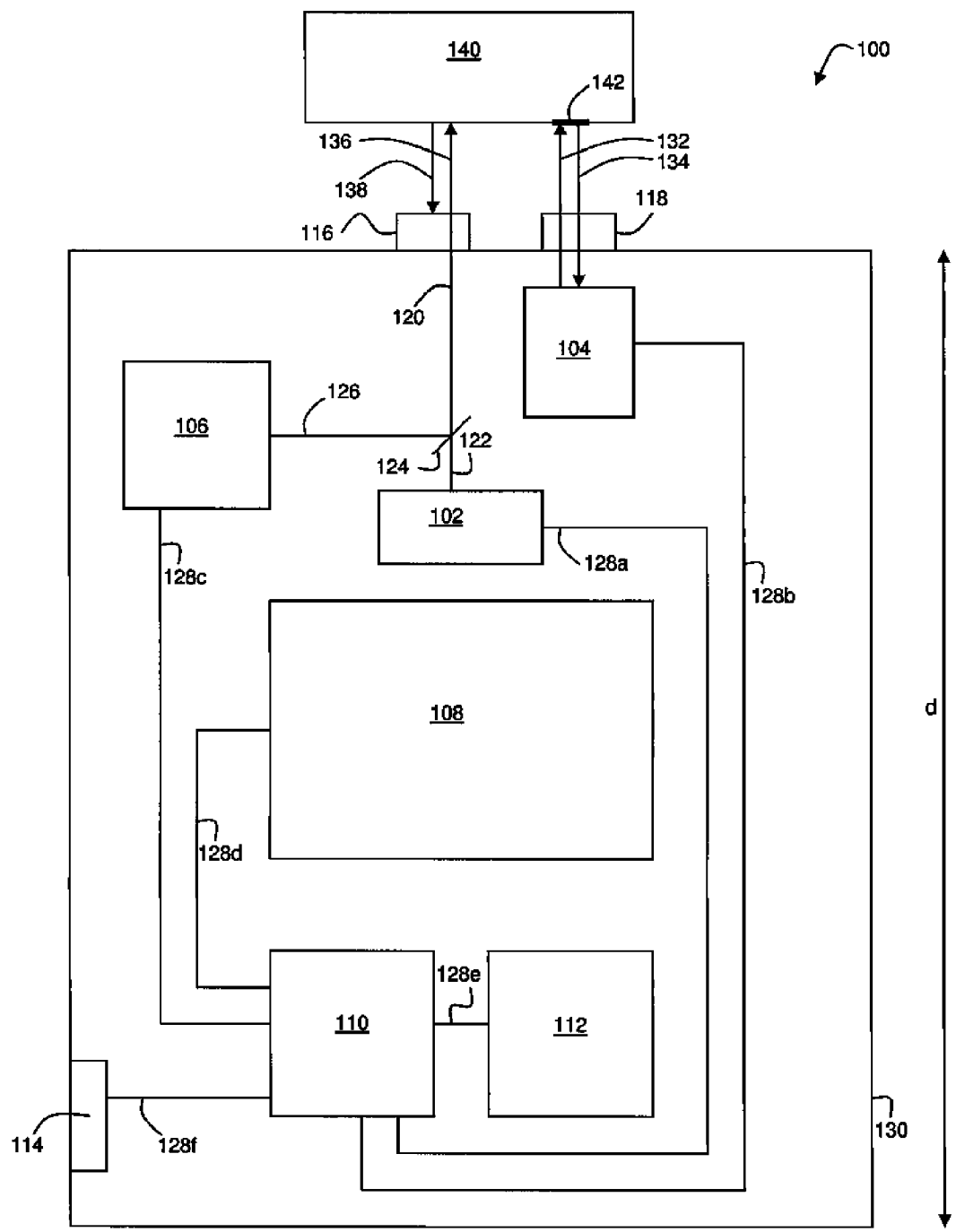
FIG. 1 is a schematic diagram of an embodiment of a scanning system.

A wide range of applications exist for scanning systems, including detection of prohibited substances at airports and in other secure and/or public locations, authentication of pharmaceutical compounds and chemicals, and general authentication of transported goods. To be useful in a variety of situations, it can be advantageous for handheld scanning systems to be portable (e.g., to have a hand-held form factor) and to rapidly provide accurate results.

Conventionally, when interrogating an unknown substance, a scanning system (e.g., a Raman spectrometer or Fourier Transform Infra Red Spectrometer) first scans the substance, and then compares the scan results to a database of information that includes scan results for a number of known compounds. If the system finds a match between the scan results for the unknown substance and a database entry, the system reports the matched compound. This process is referred to herein as blind scanning, because no information about the identity of the substance is available or used prior to the scanning. If the database size is relatively large, the process of comparing scan results for an unknown substance to results for hundreds or thousands of other compounds can be quite lengthy. For applications such as security screening at airports and other public locations, the time required to obtain a successful match of an unknown substance to a known compound may be too long to be of practical use.

The inventors have recognized, however, that the process of blind scanning of an unknown substance can be converted into a process of authentication of the substance, which can be completed much more rapidly. By using available information about the substance (e.g., from a container that houses the substance), an identification of the substance can be made. The process of identifying the substance includes determining a presumptive identity of the substance based upon one or more features (e.g., a bar code) of an object that contains the substance, for example.

Then, authentication of the substance can be performed, which includes determining whether the substance truly corresponds to the presumptive identity. Scanning the substance provides scan results that either corroborate or do not corroborate the presumptive identity of the substance. If the scan results are in agreement with the presumptive identity, the substance is authenticated. If not, then the substance is not authenticated, and it is likely that the substance may be different from the presumptive identity.

Typically, the process of authentication includes a relatively small number of comparisons between information measured for a substance and reference information stored in a database. In certain instances, for example, only a single comparison is performed between measured information and reference information from the database. In some instances, comparisons can be performed between measured information and multiple sets of reference information from the database. For example, the comparison between measured information and multiple sets of reference information can be performed in a two-step process, where an initial set of rapid comparisons is performed between the measured information and reference information for a few hundred compounds, and then more detailed comparisons are performed between the measured information and a small number of sets of reference information that are selected based on the initial rapid comparisons. The total number of comparisons is less (and can be significantly less) than the number of comparisons that are typically performed in a blind scanning procedure and as a result, the authentication process can be performed significantly faster than a blind identification of an unknown substance.

FIG. 1 shows a schematic diagram of a scanning system 100. System 100 includes a light source 102, a scanning module 104, a radiation processing module 106, a display 108, a processor 110, a storage unit 112, and a communication interface 114. Processor 110 is in electrical communication with light source 102, identification module 104, radiation processing module 106, display 108, storage unit 112, and communication interface 114 via communication lines 128a-f. Each of these components is enclosed within a housing 130.

In certain embodiments, identification module 104 includes a universal product code (UPC) scanner. The UPC scanner includes a light source (e.g., a light emitting diode source) that generates electromagnetic radiation. The electromagnetic radiation exits housing 130 via output port 118 as incident radiation 132. Incident radiation 132 is incident on object 140 and, in particular, on a UPC label 142 that is attached to object 140. A portion of the incident radiation is reflected back into output port 118 as reflected radiation 134, and propagates back to identification module 104. Once inside identification module 104, reflected radiation 134 is detected by a detector and analyzed by a processor to determine the UPC code on label 142. If a UPC code can be determined based on reflected radiation 134, the UPC code is transmitted to processor 110 via an electronic signal transmitted on communication line 128b.

Processor 110 then outputs a signal to display 108, and display 108 outputs the signal from processor 110. Typically, for example, the signal from processor 110 includes a presumptive identity of object 140 and/or a presumptive identity of a substance associated with object 140. For example, if object 140 is a container for a substance housed therein, the signal from processor 110 can include a presumptive identity of the substance housed in the container, and display 108 can display the presumptive identity of the substance.

Conversely, if a UPC code cannot be determined based on reflected radiation 134, an electronic signal indicating an inconclusive identification is transmitted to processor 110. Processor 110 can then transmit a signal which is displayed by display 108. The signal transmitted by processor 110 can include an indication that the UPC code is unreadable and/or unknown. Alternatively, or in addition, the signal from processor 110 can include a prompt to a system operator to attempt the identification process (e.g., by re-scanning the UPC label) again.

Light source 102 includes a laser diode source that is configured to generate electromagnetic (EM) radiation that is used to scan object 140. Typically, for example, the EM radiation has a center wavelength in the near-infrared region of the EM spectrum. Radiation generated by light source 102 is coupled via fiber optic cable 122 through dichroic beamsplitter 124 and into fiber optic cable 120. The radiation is transported via fiber optic cable 120 to output port 116, and exits housing 130 as incident scan radiation 136. Incident scan radiation 136 is incident on object 140, and a portion of the incident scan radiation is returned as emitted radiation 138. Emitted radiation 138 enters output port 116 and is coupled into fiber optic cable 120 and transported to dichroic beamsplitter 124. Dichroic beamsplitter 124 redirects emitted radiation 138 into fiber optic cable 126, which transports emitted radiation 138 into radiation processing module 106.

In some embodiments, radiation generated by light source 102 is not coupled into fibers as shown in FIG. 1. Instead, incident scan radiation 136 generated by light source 102 propagates through air to reach output port 116. Similarly, emitted radiation 138 can enter housing 130 via output port 116, and thereafter propagate through air to reach radiation processing module 106.

Radiation processing module 106 analyzes emitted light 138 to determine one or more properties of object 140 (or of a substance associated with object 140, such as a substance within object 140). For example, radiation processing module 106 can be configured to determine a Raman spectrum of a substance within object 140. The Raman spectrum is communicated to processor 110 via an electronic signal transmitted by radiation processing module 106 along communication line 128*c*.

In general, radiation processing module 106 includes various optical, mechanical, and electronic elements that can be used to analyze emitted radiation 138. For example, radiation processing module 106 can include one or more elements for dispersing EM radiation into a plurality of component wavelengths such as gratings and/or prisms. Radiation processing module 106 can also include various lenses and/or mirrors for collimating, focusing, and re-directing EM radiation, one or more filter elements for reducing radiation intensity, and one or more beamsplitting elements for dividing a radiation beam into two beams. Radiation processing module 106 also typically includes electronic components such as radiation detectors (e.g., CCD cameras, photodiodes and/or photodiode arrays) and an electronic processor.

Storage unit 112 typically includes a re-writable persistent flash memory module. The memory module is configured to store a database that includes a library of information about various objects and/or substances. The library includes information such as Raman spectra for various substances, for example. Processor 110 can retrieve Raman spectra from storage unit 112 via a request transmitted on communication line 128*e*. Storage unit 112 can also store settings and other configuration information for system 100 such as default scanning parameters and operating settings. Other storage media can also be included in storage unit 112, including various types of re-writable and non-rewritable magnetic media, optical media, and electronic memory.

Communication interface 114 includes a wireless transmitter/receiver unit that is configured to transmit signals from processor 110 to other devices, and to receive signals from other devices and communicate the received signals to processor 110. Typically, for example, communication interface 114 permits processor 110 to communicate with other devices—including other scanning systems and/or computer systems—via a wireless network that includes multiple devices connected to the network, and/or via a direct connection to another device. Processor 110 can establish a secure connection (e.g., an encrypted connection) to one or more devices to ensure that signals can only be transmitted and received by devices that are approved for use on the network.

Processor 110 communicates with a central computer system to update the database of information stored in storage unit 112. Processor 110 is configured to periodically contact the central computer system to receive updated database information. The updated database information can include, for example, a list of prohibited substances and/or a list of UPC codes and associated substances. Processor 110 can also communicate with other scanning systems to broadcast alert messages when certain substances—such as substances on the list of prohibited substances—are detected, for example.

Housing 130 has a hand-held form factor to ensure that system 100 is portable and, as a hand-held device, can be used in a wide variety of applications. In certain embodiments, for example, a maximum dimension d of housing 100 is less than 36 cm, a volume of housing 100 is less than 2000 $cm^3$, and a total mass of system 100 is less than 3 kg. Housing 130 is a rugged housing that protects the various components of system 100 against breakage if housing 130 is dropped or otherwise subjected to trauma by the system operator. To ensure that housing 130 is a rugged housing, the housing includes shock-absorbing inserts that reduce the strength of external forces applied to components of system 100. Housing 130 can also include shock-absorbing external pads (e.g., formed of rubber) to cushion forces that are generated during rough handling. Even with these features, the total mass of system 100 is less than 3 kg.

Figure 2:
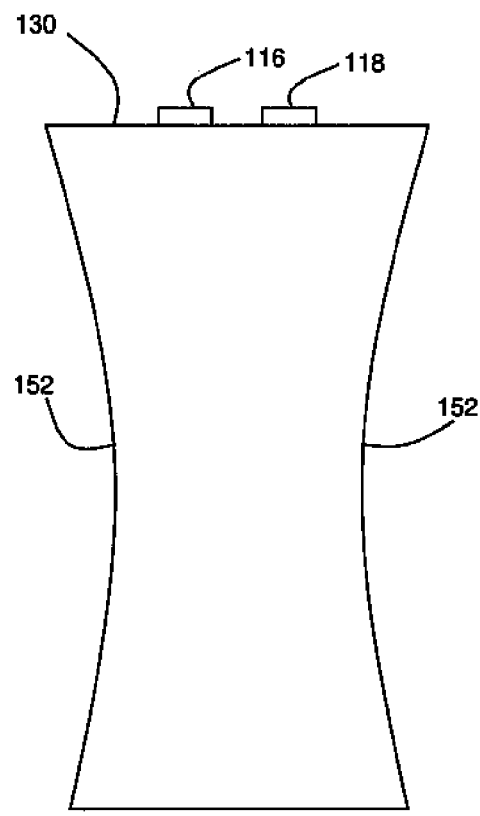
FIG. 2 is a schematic diagram of an embodiment of a housing for a scanning system.
Figure 3:
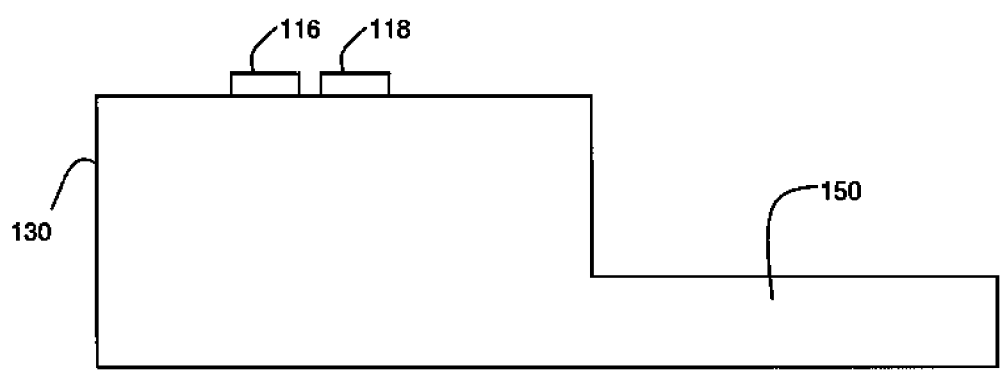
FIG. 3 is a schematic diagram of another embodiment of a housing for a scanning system.

For ergonomic handling of system 100, housing 130 can include a handle 150 or a gripping portion to allow a system operator to comfortably manipulate the system. Alternatively, or in addition, in some embodiments, housing 130 can include contours that facilitate handling of system 100 with only one hand. FIGS. 2 and 3 show two different embodiments of housing 130. In FIG. 2, housing 130 includes contours 152 that facilitate gripping of the housing in the region of the contours, due to the reduced width of the housing. In FIG. 3, housing 130 includes a handle 150 that permits efficient one-handed operation of system 100.

Figure 4:
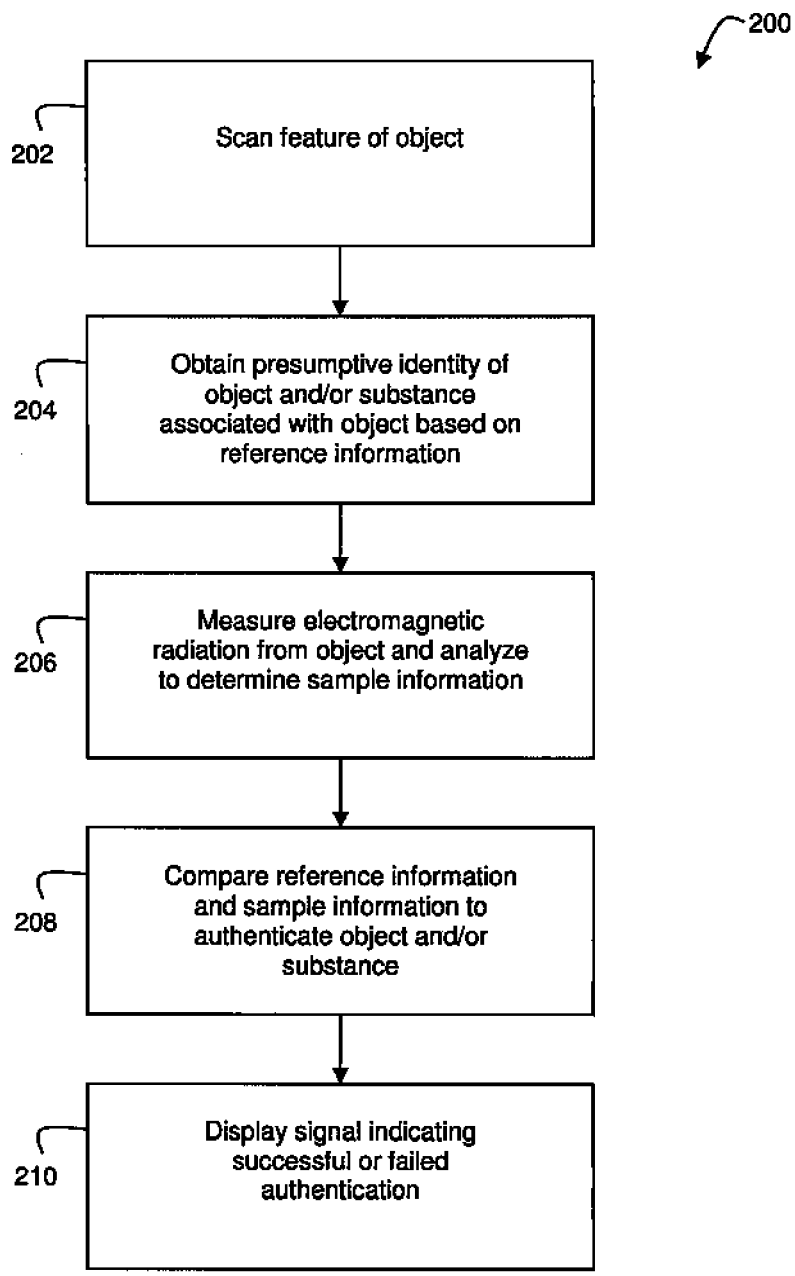
FIG. 4 is a flow chart showing steps in authenticating an object.

FIG. 4 shows a flow chart 200 that includes a series of steps performed by system 100 to authenticate an object or a substance associated therewith. In general, a system operator holds system 100—and output ports 116 and 118 in particular—in relatively close proximity (e.g., within about 12 inches) to object 140. After an initiation step from the system operator (e.g., a button-push on a user interface), in a first step 202, a feature of object 140 is scanned. As discussed above in connection with identification module 104, object 140 includes a UPC label 142 that provides information about a substance inside object 140. Identification module 104 directs incident radiation onto UPC label 142 and measures reflected radiation from the label.

In step 204, the substance within object 140 is identified on the basis of the reflected radiation measured by identification module 104. As discussed above, the process of identification includes determining a presumptive identity of object 140 and/or a substance therein. Identification module 104 analyzes the reflected radiation and determines a UPC code for the substance within object 140. The UPC code is transmitted to processor 110 via communication line 128*b*. Processor 110 sends a lookup request to a UPC code database stored in storage unit 112 to determine a presumptive identity of the substance in object 140 based on the UPC code. When a match to the UPC code is found in the UPC code database, processor 110 displays the matched compound to a system operator via display 108.

If identification module 104 cannot determine a UPC code based on the reflected radiation, processor 110 displays a signal via display 108 that indicates that scanning of the UPC label failed, and optionally prompts the system operator to repeat the scanning of the UPC label. If an identification of the substance within object 140, including determining a presumptive identity of the substance, cannot be made because the UPC code determined from the reflected radiation does not match any code in the UPC code database, processor 110 displays a signal via display 108 that indicates that the UPC code is unknown to system 100.

In step 206, EM radiation emitted from object 140 (e.g., by the substance within object 140) is measured and analyzed to determine sample information about the substance. As discussed above in connection with FIG. 1, system 100 is configured to measure Raman spectra of objects. Light source 102 directs EM radiation to be incident on object 140. Typically, object 140 is a container that conventionally holds the substance and is at least partially transmissive of the incident EM radiation, which is then absorbed by the substance within object 140. The incident EM radiation couples to one or more Raman-active modes in the substance, exciting the modes. The substance emits Raman-shifted EM radiation (e.g., emission of Raman-shifted EM radiation occurs due to scattering of the incident EM radiation by the substance), which is also emitted through the walls of object 140 as emitted light 138.

The Raman-shifted emitted light 138 is measured and analyzed by radiation processing module 106.

Radiation processing module 106 derives a Raman spectrum of the substance from emitted light 138. The Raman spectral information is transmitted to processor 110 via communication line 128c. Referring again to FIG. 4, processor 110 is configured to retrieve a reference Raman spectrum that corresponds to the identified compound in step 204 from storage medium 112. Following retrieval of the reference information, processor 110 compares the reference Raman spectral information to the measured Raman spectral information (from step 206) and determines whether the measured Raman spectral information corresponds to the substance identified in step 204.

If the measured Raman spectral information corresponds to the presumptive identity of the substance determined during the identification process, system 100 considers the substance authenticated—that is, the substance is considered by the system to correspond to UPC label 142 attached to object 140. When authentication is complete, and if the identified substance does not correspond to a substance on the list of prohibited substances, processor 110 outputs a signal to the system operator via display 108 in step 210 of flow chart 200. The signal can include a region of display 108 that is colored green and/or a printed message. The signal indicates to the operator that the substance in object 140 does indeed correspond to the UPC label on the object, and that the substance does not appear on the prohibited substances list.

If the measured Raman spectral information does not correspond to the presumptive identity of the substance in step 210, processor 110 outputs a signal to the system operator via display 108 that indicates that the substance was not successfully authenticated. The signal can include, for example, a region of display 108 that is colored red and/or a printed message. The signal indicates to a system operator that the substance in object 140 may not correspond to the UPC label on the object. In many applications, the signal can also indicate to the system operator that the substance should be investigated in more detail, and possibly confiscated from its bearer. In some embodiments, the signal can also offer the system operator the option to operate system 100 in a blind scanning mode; that is, system 100 can perform comparisons between the measured Raman spectral data for the substance and reference Raman spectral data stored in storage unit 112 for a relatively large number of compounds until either a prospective match is obtained, or the reference information in storage unit 112 is exhausted.

In general, the printed messages that are displayed by processor 110 on display 108 can be selected based on the application of system 100 to scanning particular types of objects and/or substances. For example, in certain embodiments, system 100 can be used for non-security scanning of industrial materials and/or products, or scanning of pharmaceutical compounds and/or precursor compounds. System 100 can be configured to display a printed "Pass" message if authentication is successful, or a printed "Fail" message if authentication is not successful.

In security screening applications, a list of prohibited substances can be stored in storage unit 112, and the presumptive identity of object 140 and/or an associated substance can be compared to the list of prohibited substances following the identification process. If the presumptive identity appears on the list of prohibited substances, a red-colored signal that includes a message such as "Alarm" can be displayed to the system operator. The signal can be displayed prior to exposing the object and/or substance to EM radiation.

If the presumptive identity does not appear on the list of prohibited substances, authentication proceeds as discussed above. If authentication is successful, a green-colored signal that includes a message such as "Clear" can be displayed to the system operator. If authentication fails, a red-colored signal that includes a message such as "Alarm" can be displayed to the system operator. Other information can also be displayed such as, for example, one or more reasons why the "Alarm" message was displayed (e.g., due to a failed comparison between measured and reference Raman spectral information). In certain embodiments, processor 110 can determine (e.g., based on the comparison between the measured and reference Raman information, and/or based on other information) that a substance in object 140 appears to have been altered in a manner that may pose a security risk. For example, the substance can be a commercial product, such as a household product, that has been modified in some way. Information can be displayed to a system operator that indicates that system 100 has detected that a substance in the object appears to have been altered.

Embodiments of the systems and methods disclosed herein have been described in connection with FIGS. 1-4 above. However, other embodiments are also possible. For example, in the systems and methods disclosed, a presumptive identity of the substance in container 140 is determined by scanning a UPC label (e.g., a bar code), determining a UPC code based on the scanned label, and comparing the UPC code to a database of UPC codes to determine a presumptive identity of the substance. In general, however, a variety of different features can be scanned to determine presumptive identities of objects and/or their associated substances in the identification procedure.

In some embodiments, the feature that is scanned is a feature on the object such as a feature on a surface of the object. Exemplary features that can be scanned to determine an identity of an object include: radio-frequency identification (RFID) tags, where system 100 includes an RFID tag reader; identification numbers, where system 100 includes an optical character recognition (OCR) scanner configured to read numbers printed on the object or on a label attached thereto; alphanumeric symbols, where system 100 includes an OCR scanner configured to read the symbols; and one or more images (e.g., including one or more logos), where system 100 includes a graphical scanner configured to read the images. In certain embodiments, system 100 can include multiple different identification modules, including any combination of the devices disclosed above, for scanning features of objects (e.g., a bar code reader and an RFID tag reader).

In certain embodiments, the features that are scanned to determine a presumptive identity of the object or associated substance can includes features of the object, such as a shape of the object. For example, if the object is a container that holds a substance, the substance can be identified based on the shape of the container. Alternatively, or in addition, the container can have a label that is scanned to determine the identity of the substance in the container. The substance can be identified on the basis of the shape and/or color of the label, for example, and/or on the basis of any alphanumeric symbols and/or graphic images thereon.

In general, a variety of different numbers scanned by system 100 can be used to determine a presumptive identity of an object or an associated substance. Exemplary numbers that can be scanned include National Drug Codes, European Article Numbers, Global Trade Item Numbers, Serial Shipping Container Codes, Global Location Numbers, Global Returnable Asset Identifiers, Global Individual Asset Identifiers, and Global Service Relation Numbers.

In the embodiments disclosed above, Raman spectral data was measured from a substance within object 140 and compared to reference Raman spectral data to authenticate the substance. In general, however, a variety of different types of information can be used to authenticate an object and/or an associated substance. In general, EM radiation from light source 102 is directed to be incident on the object, and radiation emitted from the object (including, for example, radiation emitted by a substance within the object) in response to the incident radiation is measured by radiation processing module 106 and used to derive sample information.

In some embodiments, the sample information can include other information in addition to, or in the alternative to, Raman spectral information. The information can include fluorescence spectral information about the object or associated substance, infrared absorption information about the object or associated substance (including infrared absorption information determined using Fourier-transform infrared spectroscopic techniques), and dielectric information about the object or associated substance. Radiation processing module 106 can be configured to derive one or more of the above types of information about the object or substance from the emitted radiation.

In certain embodiments, the sample information can include a signal intensity at one or more wavelengths that is measured for the object or associated substance. Alternatively, or in addition, in certain embodiments, the sample information can include one or more data acquisition parameters. For example, the sample information can include an exposure time, where the exposure time corresponds to the time during which the object was exposed to incident radiation to achieve, for example, a particular value of a measured signal strength, and/or a particular value of a measured signal-to-noise ratio.

In some embodiments, the sample information can include other measured properties of the object or associated substance. For example, the sample information can include a photobleaching time for the object or substance. The photobleaching time corresponds to an elapsed during exposure of the object and/or substance to incident radiation over which an absorption coefficient of the object or substance is reduced to a predetermined value by saturation due to the incident radiation.

In certain embodiments, combinations of the different types of sample information disclosed above can be measured and compared to corresponding reference information to determine presumptive identities of objects and/or associated substances. For example, both Raman spectral information and fluorescence spectral information can be measured and compared to reference information. In general, any combination of the types of information disclosed above can be measured and used for comparison to reference information. System 100 can include components in addition to those shown in FIG. 1 to enable measurement of the various types of information. For example, system 100 can include multiple light sources 102 and/or multiple radiation processing modules 106 configured to measure multiple types of information for an object and/or substance.

In general, radiation processing module 106 can be configured to measure radiation emitted from object 140 and/or an associated substance, and to determine one or more of the types of information disclosed herein. Further, corresponding reference information can be present in storage unit 112 for retrieval by processor 110. The reference information can include Raman spectral information, infrared absorption information, fluorescence information, dielectric information, wavelength-dependent signal intensity information, one or more data acquisition parameters (e.g., exposure times, signal-to-noise ratios), photobleaching times, and other information. The information can also include composition information about substances, concentration limits for components of substances, and other information that can be used to determine a presumptive identity of an object and/or substance based on a scanned feature of the object, such as databases of UPC codes, RFID codes, and standard number codes.

System 100, as described above, is configured to direct near-infrared incident radiation with a wavelength of about 785 nm to be incident on sample 140. Generally, however, radiation in a variety of different wavelength bands, including ultraviolet radiation, visible radiation, and infrared radiation, can be used. Typically, EM radiation generated by light source 102 includes a distribution of wavelengths and has a center wavelength associated with the distribution. In some embodiments, the center wavelength of the incident radiation is 850 nm or less (e.g., 825 nm or less, 800 nm or less, 775 nm or less, 750 nm or less, 725 nm or less, 700 nm or less, 675 nm or less, 650 nm or less, 625 nm or less, 600 nm or less, 575 nm or less, 550 nm or less, 525 nm or less, 500 nm or less, 475 nm or less, 450 nm or less, 400 nm or less, 375 nm or less, 350 nm or less, 325 nm or less, 300 nm or less, 275 nm or less, 250 nm or less) and/or 170 nm or more (e.g., 180 nm or more, 190 nm or more, 200 nm or more, 210 nm or more, 220 nm or more, 230 nm or more, 240 nm or more). In certain embodiments, the center wavelength of the incident radiation is between 200 nm and 400 nm (e.g., between 220 nm and 350 nm, between 230 nm and 300 nm, between 240 nm and 300 nm, between 240 nm and 280 nm, between 240 nm and 260 nm). In some embodiments, the center wavelength of the incident radiation is between 650 nm and 850 nm (e.g., between 700 nm and 800 nm, between 750 nm and 800 nm).

Radiation in other regions of the EM spectrum can also be directed to object 140 by light source 102. For example, radiation in one or more of the microwave region, the radiowave region, the terahertz region, the x-ray region, and the gamma ray region of the EM spectrum can be used to interrogate object 140.

In certain conventional Raman spectrometers, when radiation in the near-infrared region of the EM spectrum is incident on object 140, an intensity of the incident radiation, measured at the position of object 140, is between 100 mW and 1 W. These relatively high radiation intensities can cause problems, however, if object 140 contains a substance that is heat- or light-sensitive. In particular, explosive decomposition of certain energetic materials can be initiated by heat or light provided by EM radiation of this intensity.

The inventors have recognized, however, that certain processes such as Raman scattering are more efficient at shorter wavelengths (e.g., ultraviolet wavelengths). As a result, by using shorter wavelength incident EM radiation, the incident radiation intensity can be reduced and accurate, reproducible results can still be obtained. Further, by reducing the radiation intensity, there is less potential for inadvertent damage to the eyes of a system operator or another person nearby due to exposure to the incident radiation. In addition, by reducing the radiation intensity, fluorescence emission from certain substances is reduced. Because fluorescence emission can interfere with Raman spectral measurements, reducing the intensity of the incident radiation can enable more accurate Raman measurements. In particular, in some embodiments, an intensity of the incident radiation can be 10 mW or less (e.g., 8 mW or less, 6 mW or less, 4 mW or less, 3 mW or less, 2 mW or less, 1 mW or less).

In general, however, incident radiation can have a wide range of intensities. In some embodiments, the incident radiation intensity is 1 mW or more (e.g., 5 mW or more, 25 mW or more, 100 mW or more, 250 mW or more, 500 mW or more, 750 mW or more, 1 W or more, 1.5 W or more). In certain embodiments, the incident radiation intensity is between 1 mW and 1.5 W (e.g., between 1 mW and 10 mW, between 1 mW and 5 mW, between 100 mW and 500 mW, between 500 mW and 1.5 W, between 500 mW and 1 W).

Processor 110 is configured to output a signal to display 108 to indicate whether object 140 or a substance associate therewith has been successfully authenticated. In some embodiments, in addition to the displayed signal, processor 110 can be configured to output other signals. For example, system 100 can include an audio output device such as a speaker, and processor 110 can output an audio signal via the audio output device that indicates either a successful or failed authentication. If an object or its associated substance appears on the list of prohibited substances, processor 110 can output an audio signal, which can be a different signal from the signal indicating a successful or failed authentication.

Alternatively, or in addition, processor 110 can be configured to output a signal to one or more devices via communication interface 114. The one or more devices can include other hand-held scanner systems, and the signal can be an alert signal that indicates a failed authentication and/or detection of a prohibited substance. The signal can be broadcast wirelessly to the other devices. Alternatively, or in addition, the one or more devices can include a central computer system which monitors multiple scanning systems, including system 100. The central computer system can keep and update records of the time, location, and presumptive identity of substances involved in failed authentications and/or the detection of prohibited substances. The central computer system can also broadcast alerts to other systems and/or to human (e.g., security personnel) who may intervene following a failed authentication and/or detection of a prohibited substance.

In general, as discussed above, one or more devices can be connected to one another over a wireless network. The connections can be insecure or secure connections, and a portion of the network can include the internet. In certain embodiments, system 100 can be connected to other devices over other types of networks, including isolated local area networks and/or cellular telephone networks. The connection can be a wireless connection or a wired connection. Signals, including alert messages, can be transmitted from processor 110 to a variety of devices such as cellular telephones and other network-enabled devices that can alert personnel in the event that authentication of an object or its associated substance fails, or in the event that a prohibited substance is detected.

Typically, system 100 includes a control panel (not shown in FIG. 1) that enables a system operator to set configuration options and change operating parameters of system 100. In some embodiments, system 100 can also include an internet-based configuration interface that enables remote adjustment of the systems configuration options and operating parameters. The interface can be accessible via a web browser, for example, over a secured or insecure network connection. The internet-based configuration interface permits remote updating of scanning systems by a central computer or another device, ensuring that all scanners that are operated in a particular location or for a particular purpose have similar configurations. The internet-based interface can also enable reporting of scanner configurations to a central computer system, for example, and can enable tracking of the location of one or more scanning systems.

Scanning objects generally should be performed relatively rapidly so as not to unduly impede the flow of people and cargo into secure facilities such as airports. In general, the process of authenticating an object or substance is significantly faster than blind scanning procedures. In some embodiments, a total elapsed time between the initiation of identifying a feature of the object (step 202 in FIG. 4) and the end of the comparison in step 208 to determine whether the substance is authenticated is 60 seconds or less (e.g., 45 seconds or less, 30 seconds or less, 20 seconds or less, 10 seconds or less, 5 seconds or less, 1 second or less).

In some embodiments, system 100 is configured to determine a concentration of a substance in object 140. To determine a concentration of the substance, a presumptive identity of the substance is first determined according to steps 202 and 204 of FIG. 4. Then, in step 206, an emitted radiation intensity from the substance is measured at one or more wavelengths. The radiation intensity information is transmitted to processor 110. Processor 110, on the basis of the identification of the substance, retrieves reference information from storage unit 112 that includes emitted radiation intensities at one or more wavelengths for one or more known concentrations of the substance. Processor 110 then compares the measured radiation intensities to the reference information to make a quantitative determination of the concentration of the substance. Determining the concentration can include, for example, interpolating and/or extrapolating measured intensities for known concentrations of the substance. Alternatively, or in addition, determining the concentration can include determining a ratio of measured intensities and intensities from the reference information, and assessing the concentration of the substance based upon the ratio.

In certain embodiments, processor 110 can be configured to output a signal if a concentration determined for the substance does not fall within a predetermined range of concentrations conventionally associated with the substance. For example, reference information stored in storage unit 112 can include a range of acceptable concentrations of the substance. If a concentration of the substance is determined to fall outside the acceptable range (or if the concentration differs from a reference concentration of the substance by more than a predetermined amount), processor 110 can output a signal to display 108 (and, optionally, one or more other signals such as audio signals and broadcast messages to other devices). The signal can include one or more words, such as the word "Alarm", and can include a colored region of display 108 (e.g., a red-colored region).

In some embodiments, the substance associated with object 140 includes two or more components, and system 100 can be configured to determine concentrations of the two or more components. The process for determining concentrations of two or more components is similar to the process for determining the concentration of a single substance. Following determination of presumptive identities of each of the components by scanning a feature of object 140 (and, in certain embodiments, referencing a database stored on storage unit 112 to determine the components based on the scanned feature), emitted radiation intensities are measured by radiation processing module 106 for each of the components. The measured radiation intensities are compared to reference information (e.g., by determining ratios of the reference and measured intensities) to quantitatively determine concentrations of the components. Processor 110 can be configured to output a signal that indicates whether a concentration of at least one of the components is larger than a reference concentration associated with the component, or if a concentration of at least one of the components differs from a reference concentration by more than a predetermined amount. Alternatively, or in addition, processor 110 can be configured to compare concentrations of the two or more components (e.g., by determining ratios of the concentrations of the components), and to output a signal that indicates whether a ratio of any two of the components differs from an expected value of the ratio by more than a predetermined amount, where the expected value of the ratio is based on reference concentration information for the components stored in storage unit 112.

In some embodiments, processor 110 can be configured to adjust a total measurement time of system 100. For example, light source 102 and radiation processing module 106 are typically configured to make multiple measurements of emitted radiation from object 140, where successive accumulated data is combined to build up a signal that represents the object or an associated substance. The multiple measurements can be continued, for example, until a desired signal-to-noise ratio or a desired signal intensity is achieved. However, not all substances require the same total measurement time to achieve a particular value of signal-to-noise ratio or signal intensity. Certain substances generate stronger signals than other substances. Thus, system 100 can be configured to perform only one or a small number of scans of object 140 with EM radiation from light source 102. Processor 110 can compare sample information (Raman spectral information, infrared absorption information, fluorescence information, or other sample information) determined from the one or a small number of scans to reference information stored in storage unit 112. On the basis of the comparison, processor 110 can adjust the total measurement time over which radiation emitted by object 140 is measured. Typically, for example, processor 110 shortens the total measurement time by reducing the number of scans of object 140 performed by radiation processing unit 106.

In certain embodiments, processor 110 can be terminate scanning of object 140 based on one or a small number of initial scans. For example, the identity of an object or a substance associated therewith may preclude certain features from appearing in measured information such as spectral data for the object or substance. If an initial scan or a small number of initial scans reveal features in the measured information that are incompatible with the presumptive identity of the object or substance, processor 110 can be configured to terminate further scanning of the object or substance, and to display a message indicating that authentication of the object or substance failed.

Conversely, in certain embodiments, processor 110 can be configured to increase a total measurement time for an object or substance that typically generates relatively weak signals. Processor 110 can determine whether the signals generated by the object or associated substance are relatively weak based on one or more initial scans, and/or based on reference information stored in storage unit 112.

System 100 can be applied to authenticate a large variety of different substances including pharmaceutical compounds (and precursors thereof), narcotics, industrial compounds, explosives, energetic materials (e.g., TNT, RDX, HDX, and derivatives of these compounds), chemical weapons (and portions thereof), household products, plastics, white powders, solvents (e.g., alcohols, acetone), nerve agents (e.g., soman), oils, fuels, pesticides, peroxides, beverages, and toiletry items (e.g., soaps and/or shampoos, mouthwash, shave cream, toothpaste, perfumes, nail polish, skin creams, and other topical agents). In general, system 100 can be configured to authenticate a large number of substances that may pose a threat to safety in public and/or secure locations such as airports and other transportation hubs, government buildings, and large public buildings such as office towers. System 100 can authenticate substances in a variety of physical forms and states, including solid substances, liquid substances, gaseous substances, and substances present as gels and/or slurries. System 100 can be applied to detect and/or authenticate substances that appear on the ITF-40 list of most hazardous chemicals, and/or on the EPA list of chemicals in high volume production.

In some embodiments, system 100 can be configured to detect the presence of object 140 in a larger vessel before object 140 is scanned. Object 140 can be concealed, for example, in a vessel such as an item of luggage, a packing crate or box, or another vessel, and the presence of object 140 may not be known to a human operator of system 100. System 100 can include a detection module that includes an EM radiation source such as a laser source which directs incident EM radiation to be incident upon the vessel. The detection module also includes a detector and a processing unit for receiving radiation emitted by the vessel in response to incident radiation from the radiation source, and detecting object 140 based on the received radiation.

The incident radiation provided by the detection module can include radiation in one or more regions of the EM spectrum, including the gamma ray region, the x-ray region, the ultraviolet region, the terahertz region, the infrared region, the radiowave region, and the microwave region. The detector that measures emitted radiation from the vessel can be configured to measure emitted radiation intensity (e.g., a CCD detector, or a photodiode-based detector). In certain embodiments, the detector can be configured to operate as a tomographic detector.

Alternatively, in some embodiments, system 100 can be configured to receive a signal from a separate scanning system that scans the vessel and identifies the presence of object 140. The signal received from the separate scanning system alerts an operator of system 100 that an object within the vessel exists, and should be removed and scanned by the operator.

Both identification module 104 and light source 102 provide incident radiation that is used to illuminate object 140. In the embodiments disclosed above, identification module 104 includes one or more light-emitting diodes that provide incident radiation, and light source 102 includes one or more laser diodes that provide incident radiation. In general, a variety of different elements can be used in identification module 104 and light source 102 to provide incident light. In some embodiments, for example, one or both of identification module 104 and light source 102 can include one or more light-emitting diodes, laser diodes, and lasers (e.g., gas lasers). If identification module 104 or light source 102 includes more than one element, the elements can have different spectral properties. For example, identification module 104 and/or light source 102 can include two or more light-emitting diodes, laser diodes, or lasers, each with a different spectral distribution of wavelength components. The two or more light-emitting diodes, laser diodes, or lasers can be operated at the same time to provide incident radiation with a wider spectral bandwidth than can be achieved with a single element.

In certain embodiments, the properties of incident light generated by identification module 104 and/or light source 102 can be altered by control signals from processor 110. For example, processor 110 can adjust an intensity, an exposure time, and a spectral distribution of the incident light. Processor 110 can adjust spectral properties of the incident light by activating one or more filter elements, for example. In general, each of identification module 104 and light source 102 can include lenses, mirrors, beamsplitters, filters, and other optical elements that can be used to condition and adjust properties of the generated incident light.

Housing 130 has a hand-held form factor, so that system 100 is a hand-held device. For system 100 to be portable, the mass of system 100 should not preclude a system operator from carrying system 100 by hand. In some embodiments, the total mass of system 100 is 3 kg or less (e.g., 2.8 kg or less, 2.6 kg or less, 2.4 kg or less, 2.2 kg or less, 2.0 kg or less, 1.8 kg or less, 1.4 kg or less). In certain embodiments, to ensure that system 100 is portable, the maximum dimension d of system 100 along at least one dimension of the system is less than 36 cm (e.g., less than 33 cm, less than 30 cm, less than 27 cm, less than 24 cm, less than 21 cm, less than 18 cm). In some embodiments, a volume of system 100 is less than 2000 $cm^3$ (e.g., less than 1900 $cm^3$, less than 1800 $cm^3$, less than 1700 $cm^3$, less than 1600 $cm^3$, less than 1500 $cm^3$, less than 1400 $cm^3$).

In FIG. 1, identification module 104 and the combination of light source 102 and radiation processing module 106 do not share any common optical elements. In certain embodiments, however, one or more optical elements can be shared by both identification module 104 and the combination of light source 102 and radiation processing module 106. For example, optical components such as lenses, mirrors, beamsplitters, and filters can be shared by modules 104 and 106, and light source 102.

Typically, for example, processor 110 is shared among modules 104 and 106, and light source 102, although in some embodiments, system 100 can include more than one processor (e.g., one processor dedicated to identification module 104, and another processor dedicated to radiation processing module 106). In certain embodiments, other electronic components such as power supplies, clocking and timing circuits, and signal generators can be shared by modules 104 and 106, and light source 102.

Figure 5:
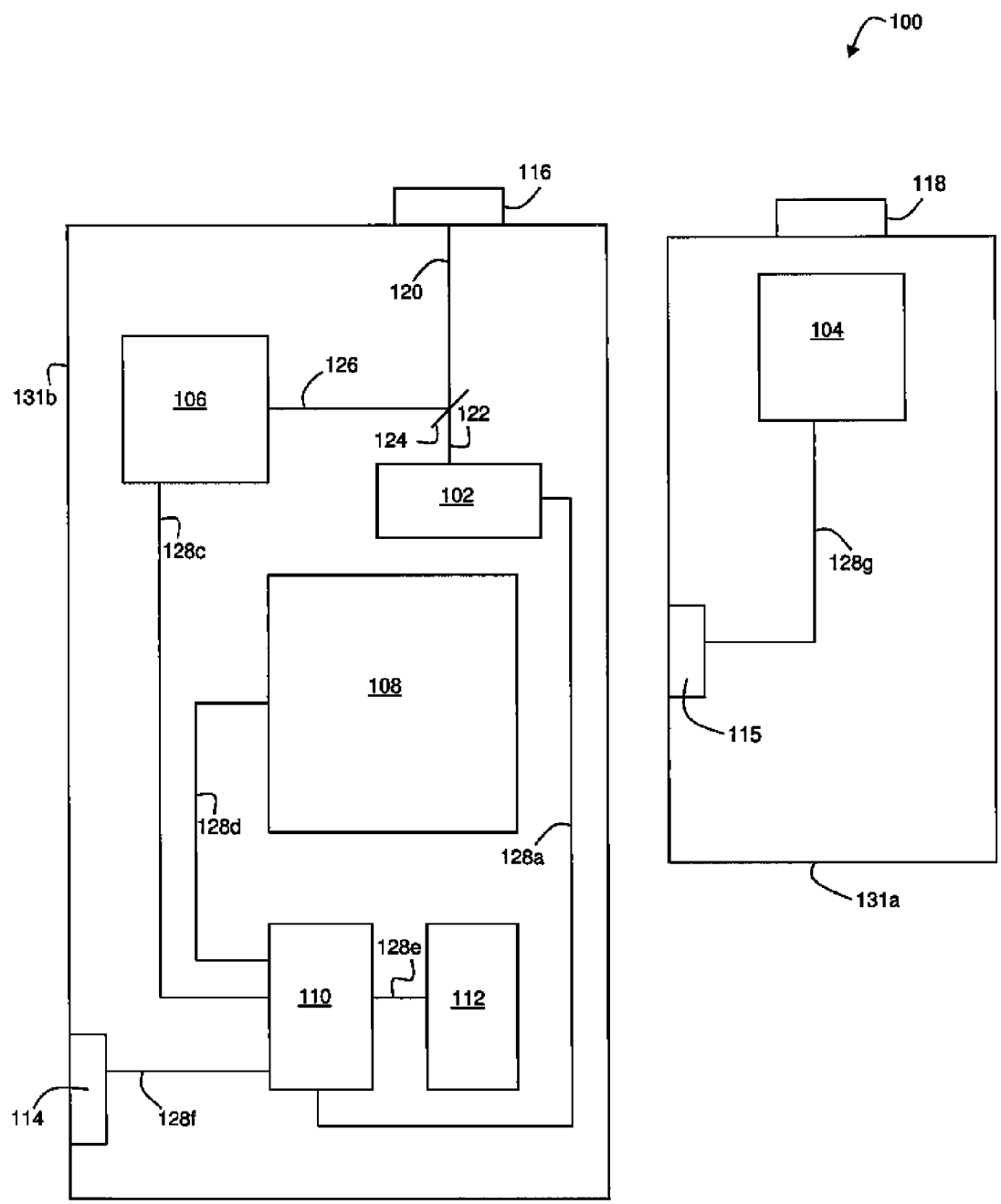
FIG. 5 is a schematic diagram of another embodiment of a scanning system.

In some embodiments, identification module 104 can be contained within a housing that is separate from a housing that contains light source 102 and radiation processing module 106. For example, FIG. 5 shows a schematic diagram of a scanning system 100 that includes two separate housings 131a and 131b. Housing 131a includes identification module 104 and a communication interface 115. Identification module 104 generally functions as disclosed above, and is connected to communication interface 115 via communication line 128g. However, following scanning a feature of object 140, information derived from the scan is communicated to processor 110 by a signal that is transmitted by identification module 104 via communication interface 115, and received by processor 110 via communication interface 114. In the embodiment shown in FIG. 5, housing 131a may have a hand-held form factor, or the housing may have a larger form factor, and can be mounted to a particular location (e.g., to a transport system that transports objects waiting to be inspected.

Processor 110 receives the information and identifies object 140 or a substance associated therewith, with reference to data stored in storage unit 112. Processor 110 can then receive sample information from radiation processing module 106 and compare the sample information to reference information retrieved from storage unit 112 on the basis of the identification, in the manner disclosed above. Typically, housing 131b, which includes light source 102, radiation processing module 106, display 108, processor 110, storage unit 112, and communication interface 114 has a hand-held form factor.

Figure 6:
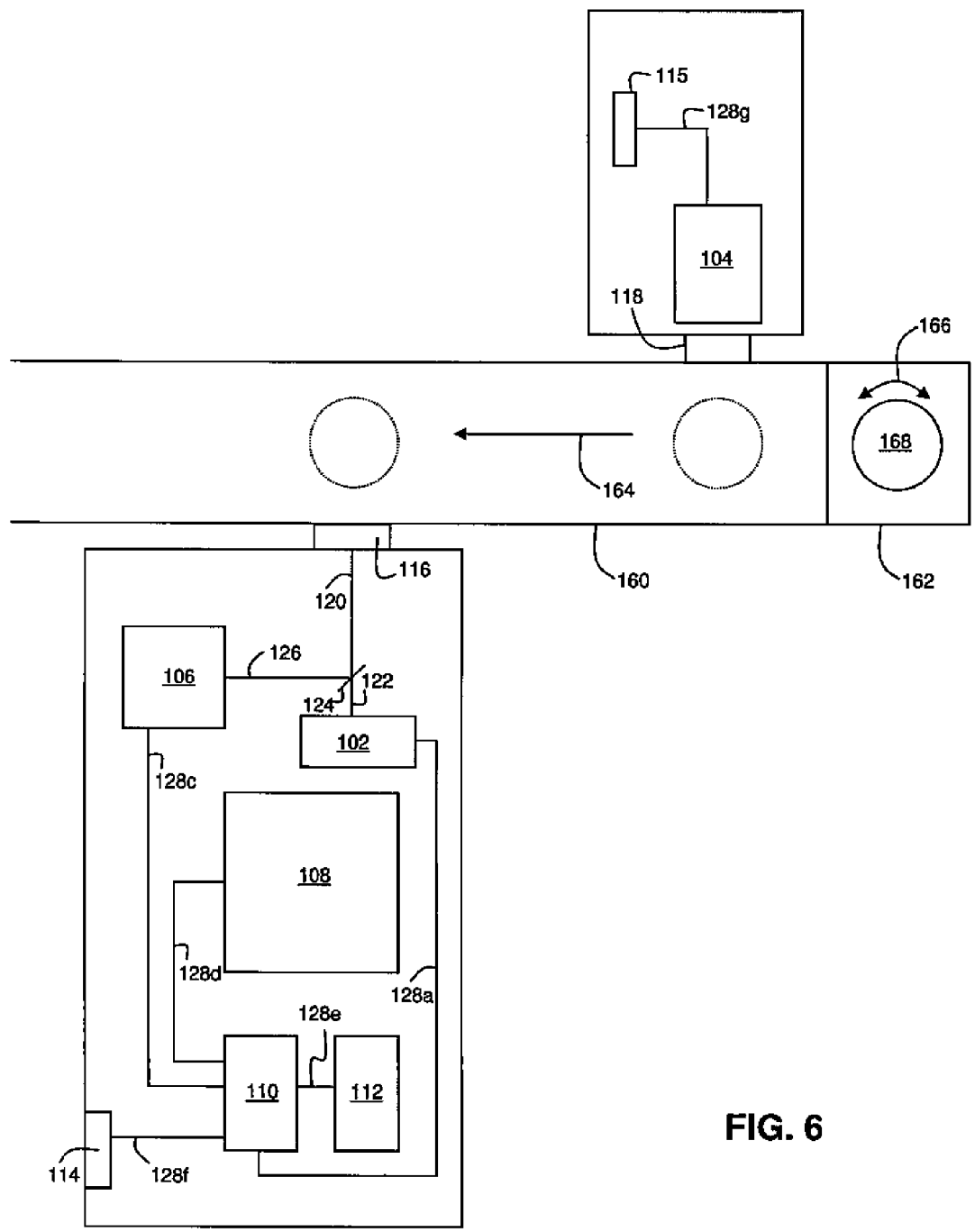
FIG. 6 is a schematic diagram of another embodiment of a scanning system.

In some embodiments, system 100 is not a handheld scanning system. For example, system 100 can be designed for table-top use in certain environments. FIG. 6 shows a schematic diagram of a scanning system 300 that is configured as a bottle scanning system. Systems of this type can be used, for example, at security checkpoints to secure locations to scan unknown objects and substances. Systems of this type can also be used in manufacturing environments, for example, to verify the contents of shipping containers either prior to use, or following production.

System 300 includes many components that have been previously discussed. System 300 also includes a conveyance mechanism 160 for transporting bottles, and a bottle manipulator 162 for bottle handling. During use, a bottle 168 is placed initially on conveyance mechanism 160 adjacent to bottle manipulator. Bottle 168 includes at least one feature—such as a UPC label or an RFID tag—that can be scanned to determine a presumptive identity of a substance inside the bottle. Bottle manipulator 162 rotates bottle 168 in the direction indicated by arrow 166 to ensure that the feature faces identification module 104.

Then, conveyance mechanism translates bottle 168 in the direction indicated by arrow 164 so that bottle 168 is adjacent to identification module 104. Identification module 104 scans one or more features of bottle 168 and, together with processor 110, determines a presumptive identity of a substance in bottle 168. Identification module 104 and processor 110 can be connected via either a wired or wireless communication link.

Conveyance mechanism 160 then translates bottle 168 again in the direction of arrow 164, until bottle 168 is positioned adjacent to output port 116. Light source 102 directs incident scan radiation 136 to impinge upon bottle 168, and radiation processing module 106 detects and processes emitted radiation 138 from bottle 168. The sample information that is obtained from emitted radiation 138 is then compared to reference information retrieved from storage unit 112 to authenticate the substance in bottle 168. As discussed previously, status and/or warning messages can be shown on display 108 by processor 110 at various times during the scanning process.

System 100 can be used for a variety of authentication-related applications. For example, system 100 can be used in airports and other transportation hubs, government buildings, and other public places to authenticate substances of indeterminate identity, and to detect prohibited substances for confiscation by authorities. Airports, in particular, restrict a variety of substances from being carried aboard airplanes. Security screening of passengers with luggage, including screening of substances of indeterminate identity among passenger belongings, can be a lengthy process. When airline passengers have scheduled flights to meet, blind scanning of unknown substances can be too time-consuming to be practical. However, system 100 can permit authentication of substances within containers (e.g., without opening the container to extract a sample) in a fraction of the time required for blind scanning. If a substance in question is authenticated and does not appear on a list of prohibited items (e.g., a list of prohibited items maintained by a security authority such as the Transportation Safety Administration), then the substance in question passes inspection. If the substance is not successfully authenticated, it can be subjected to a more rigorous inspection. If the substance appears on the list of prohibited items, it can be confiscated and the passenger carrying the item can be subjected to further scrutiny by security officers.

Law enforcement officers can also use the portable scanning systems disclosed herein to authenticate suspected samples of illegal substances such as narcotics. Accurate tests with rapid results can be performed in the field by officers on duty.

System 100 can also be used to scan a variety of industrial and pharmaceutical substances. For example, shipments of chemicals and other industrial materials can be quickly authenticated on piers and loading docks, prior to further transport and/or use of the materials. Similarly, pharmaceutical compounds and their precursors can be authenticated prior to production use and/or sale on the market.

Other Embodiments

Additional features of the methods and of the various components of system 100, including light source 102, identification module 104, radiation processing module 106, display 108, processor 110, storage unit 112, communication interface 114, and housing 130 are disclosed, for example, in the following applications, the entire contents of each of which are incorporated herein by reference: U.S. patent application Ser. No. 10/804,641 entitled "ASSEMBLY OF OPTICAL COMPONENTS AND METHOD FOR ASSEMBLING SAME", filed on Mar. 19, 2004, now published as U.S. Patent Publication No. US 2004/0240805; U.S. Pat. No. 7,110,109 entitled "RAMAN SPECTROSCOPY SYSTEM AND METHOD AND SPECIMEN HOLDER THEREFOR", issued on Sep. 19, 2006; U.S. Pat. No. 7,062,133 entitled "METHODS AND APPARATUS FOR ALIGNMENT AND ASSEMBLY OF OPTOELECTRONIC COMPONENTS", issued on Jun. 13, 2006; U.S. patent application Ser. No. 11/117,940 entitled "METHOD AND APPARATUS FOR CONDUCTING RAMAN SPECTROSCOPY", filed on Apr. 29, 2005, now published as U.S. Patent Publication No. US 2005/0248759; U.S. patent application Ser. No. 11/119,076 entitled "EXTERNAL CAVITY WAVELENGTH STABILIZED RAMAN LASERS INSENSITIVE TO TEMPERATURE AND/OR EXTERNAL MECHANICAL STRESSES, AND RAMAN ANALYZER UTILIZING THE SAME", filed on Apr. 29, 2005, now published as U.S. Patent Publication No. US 2006/0045151; U.S. patent application Ser. No. 11/215,662 entitled "UNCOOLED, LOW PROFILE, EXTERNAL CAVITY WAVELENGTH STABILIZED LASER, AND PORTABLE RAMAN ANALYZER UTILIZING THE SAME", filed on Aug. 30, 2005, now published as U.S. Patent Publication No. US 2006/0088069; U.S. patent application Ser. No. 11/119,139 entitled "LOW PROFILE SPECTROMETER AND RAMAN ANALYZER UTILIZING THE SAME", filed on Apr. 30, 2005, now published as U.S. Patent Publication No. US 2006/0044557; U.S. patent application Ser. No. 11/215,526 entitled "USE OF FREE-SPACE COUPLING BETWEEN LASER ASSEMBLY, OPTICAL PROBE HEAD ASSEMBLY, SPECTROMETER ASSEMBLY AND/OR OTHER OPTICAL ELEMENTS FOR PORTABLE OPTICAL APPLICATIONS SUCH AS RAMAN INSTRUMENTS", filed on Aug. 30, 2005, now published as U.S. Patent Publication No. US 2006/0170917; U.S. Pat. No. 7,254,501 entitled "SPECTRUM SEARCHING METHOD THAT USES NON-CHEMICAL QUALITIES OF THE MEASUREMENT", issued on Aug. 7, 2007; U.S. patent application Ser. No. 11/475,582 entitled "METHOD AND APPARATUS FOR CONDUCTING RAMAN SPECTROSCOPY", filed on Jun. 27, 2006, now published as U.S. Patent Publication No. US 2007/0002319; U.S. patent application Ser. No. 11/593,966 entitled "UNCOOLED EXTERNAL CAVITY LASER OPERATING OVER AN EXTENDED TEMPERATURE RANGE", filed on Nov. 7, 2006, now published as U.S. Patent Publication No. US 2007/0116069; and U.S. Pat. No. D534,446 entitled "HANDHELD INSTRUMENT", issued on Jan. 2, 2007.

Other embodiments are in the claims.

What is claimed is:

1. A method, comprising:
   using a first electronic device, scanning a feature of an object and based on the scanned feature, providing reference information about a substance that may be associated with the object;
   using a second electronic device to measure electromagnetic radiation emitted from the object and based on the measured electromagnetic radiation determining sample information; and
   comparing the sample information and the reference information to determine whether the substance is associated with the object.

2. The method of claim 1, wherein the object comprises a container that conventionally holds the substance.

3. The method of claim 2, wherein the feature comprises a feature on the container.

4. The method of claim 2, wherein the feature comprises a shape of the container.

5. The method of claim 1, further comprising outputting an electrical signal based on the comparison.

6. The method of claim 5, wherein the signal comprises information about an identity of the object or substance.

7. The method of claim 5, wherein the outputting comprises transmitting a signal over a communication link.

8. The method of claim 5, further comprising displaying information to a person based on the electrical signal, wherein displaying the information comprises displaying a message indicating an alarm condition or a no-alarm condition.

9. The method of claim 8, wherein the message indicating the no-alarm condition corresponds to the object or substance not appearing on a list of prohibited items.

10. The method of claim 8, wherein the message indicating the alarm condition corresponds to the object or substance appearing on a list of prohibited items.

11. The method of claim 8, wherein the message indicating the alarm condition corresponds to a determination that the object does not comprise the substance associated with the object.

12. The method of claim 1, wherein the feature comprises a bar code.

13. The method of claim 1, wherein the feature comprises a radio-frequency identification tag.

14. The method of claim 1, wherein measuring electromagnetic radiation emitted from the object comprises directing radiation to be incident on the object, and measuring radiation emitted by the object in response to the incident radiation.

15. The method of claim 1, wherein providing reference information comprises obtaining information from a database based on the scanned feature.

16. The method of claim 15, wherein the reference information is based on an infrared absorption spectrum of the object or substance, a fluorescence spectrum of the object or substance, a Raman spectrum of the object or substance, or on dielectric information about the object or substance.

17. The method of claim 15, wherein the reference information comprises a measured signal intensity at one or more wavelengths from the object or substance.

18. The method of claim 15, wherein the reference information comprises one or more data acquisition parameters related to the object or substance.

19. The method of claim 1, wherein providing sample information comprises determining an infrared absorption spectrum, determining a fluorescence spectrum, or determining a Raman spectrum.

20. The method of claim 1, wherein a total elapsed time between a beginning of the scanning and an end of the comparing is 10 seconds or less.

21. The method of claim 1, further comprising determining a concentration of the substance, wherein determining the concentration comprises providing reference information that comprises an expected emitted radiation intensity from the substance, measuring an emitted radiation intensity from the substance, and comparing the expected and measured intensities to determine the concentration.

22. The method of claim 21, further comprising outputting an electrical signal indicating an alarm condition or a no-alarm condition, wherein the signal is based on the concentration, wherein the no-alarm condition corresponds to a concentration that differs from a concentration derived from the reference information by less than a predetermined amount, and wherein the alarm condition corresponds to a concentration that differs from the concentration derived from the reference information by more than a predetermined amount.

23. The method of claim 1, wherein the substance is a pharmaceutical compound, a precursor of a pharmaceutical compound, an industrial compound, a narcotic, an explosive, an energetic material, a household product, or a portion of a chemical weapon.

24. A system, comprising:
a first apparatus configured to scan a feature on an object and provide reference information about a substance that may be associated with the object, based on the scanned feature;
a second apparatus configured to measure electromagnetic radiation emitted from the object and provide sample information based on the measured electromagnetic radiation; and
an electronic processor configured to compare the sample information and the reference information to determine whether the sample information and the reference information match.

25. The system of claim 24, further comprising a housing comprising the first and second apparatus and the electronic processor.

26. The system of claim 25, wherein the housing has a hand-held form factor so that the system is a hand-held device.

27. The system of claim 24, wherein the first apparatus comprises a bar code reader.

28. The system of claim 24, wherein the first apparatus comprises a radiofrequency identification tag reader.

29. The system of claim 24, wherein the second apparatus comprises a detector configured to measure infrared radiation absorption by the object or substance, a detector configured to measure fluorescence radiation emitted by the object or substance, or a detector configured to measure a Raman spectrum of the object or substance.

30. A system, comprising:
a housing having a hand-held form factor and comprising a first apparatus, a second apparatus, and an electronic processor in communication with the first and second apparatus,
the first apparatus being configured so that during operation, the first apparatus scans an identifying feature on an object and provides reference information to the electronic processor about a substance conventionally associated with the object,
the second apparatus being configured so that during operation, the second apparatus measures electromagnetic radiation emitted from the object and provides sample information about the composition of the object to the electronic processor based on the measured electromagnetic radiation, and
the electronic processor being configured so that during operation, the electronic processor compares the sample information and the reference information to determine whether the object comprises a substance conventionally associated with the object.

* * * * *